United States Patent [19]

Banka

[11] 4,299,226
[45] Nov. 10, 1981

[54] CORONARY DILATION METHOD

[76] Inventor: Vidya S. Banka, 237 Stacey Rd., Penn Valley, Narberth, Pa. 19072

[21] Appl. No.: 64,974

[22] Filed: Aug. 8, 1979

[51] Int. Cl.³ ........................................... A61M 25/00
[52] U.S. Cl. ................................... 128/344; 128/657; 128/349 B; 128/325
[58] Field of Search ..................... 128/344, 348, 349 B, 128/349 BV, 325, 657

[56] References Cited

U.S. PATENT DOCUMENTS

| | | | | |
|---|---|---|---|---|
| 3,633,579 | 3/1969 | Alley et al. | .......................... | 128/348 |
| 3,903,885 | 9/1975 | Fuchs | .................................. | 128/348 |
| 4,077,394 | 3/1978 | McCurdy | ............................ | 128/1 D |

*Primary Examiner*—Norman Yudkoff
*Attorney, Agent, or Firm*—Benasutti Associates, Ltd.

[57] ABSTRACT

A novel coronary dilation method is disclosed wherein a guiding catheter having at least one side arm is continuously flushed with heparinized saline during the dilation process except for momentary interruptions for recording coronary pressures. In accordance with the preferred embodiment method, a dilating catheter (of a balloon-type) is inserted with the guiding catheter and is also continuously flushed through an inner lumen except for periodic pauses to record coronary pressures. A stylet having a thickness substantially thinner than the inner lumen of the dilating catheter is inserted therein, which stylet terminates 3 to 5 mm. short of the end of the catheter. The outer lumen of the dilating catheter is utilized to inject dye and saline for inflating the balloon to perform the coronary dilation. Using the method of the present invention, the patient need not be entirely heparinized nor will significant difficulties be encountered in directing the dilating catheter to the obstruction to be dilated.

5 Claims, 3 Drawing Figures

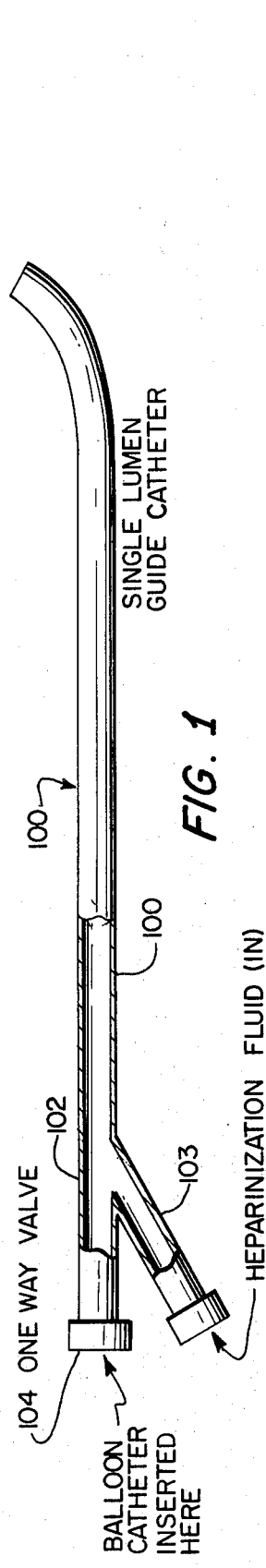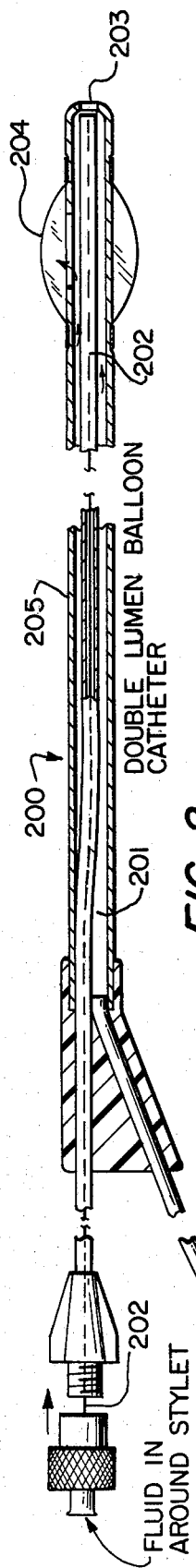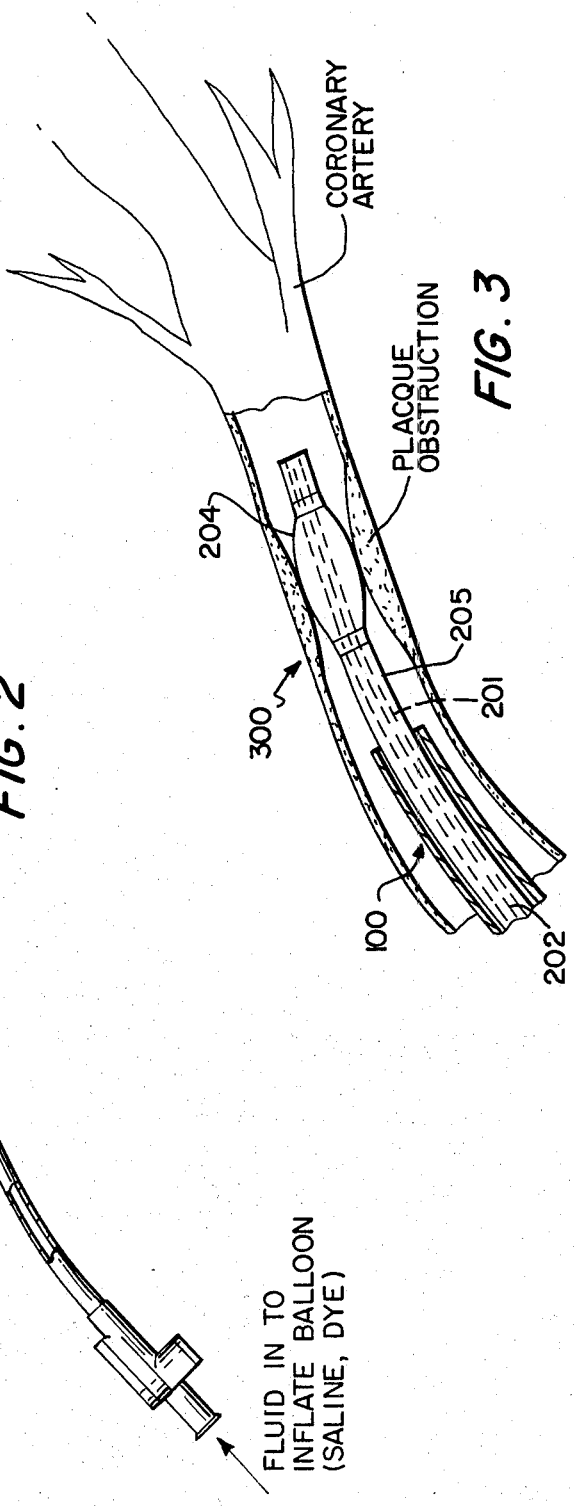

CORONARY DILATION METHOD

BACKGROUND OF THE INVENTION

The present invention relates to methods of dilating coronary arteries, and more particularly to methods utilizing balloon-type catheters to dilate arteries in the area of obstructions therein.

It has long been desired to increase the blood supply to the heart through the coronary arteries when those arteries have become clogged through the build-up of cholesterol plaque and/or other substances. Coronary bypass operations have for many years been utilized for this purpose, which operations normally include sewing segments of leg vein onto such arteries to shunt blood around blocked areas. Such coronary bypass operations have achieved considerable success in relieving symptoms associated with this condition.

More recently, a technique introduced in Switzerland by Dr. Andreas Grüntzig relies upon a balloon-type catheter which is inserted through a guide catheter to a point where the balloon portion of the catheter is disposed within a cholesterol plaque blockage. The balloon is then inflated compressing the plaque and clearing the passage. While this technique shows considerable promise, difficulties have been encountered in working the catheters through the arteries to the point of blockage. This and other complications are also likely to result as a result of the complete heparinization of the patient during the performance of the Grüntzig technique of coronary dilation. It would, of course, be desirable to improve the reliability of this technique, while at the same time decreasing risk which is attendant thereto.

SUMMARY OF THE INVENTION

The present invention provides a novel method of dilating coronary arteries using a unique combination of catheterization, flushing and guiding steps to substantially increase the safety and reliability of cardiac dilation operations. In particular, the method comprises the steps of providing a guide catheter having a pressure monitoring/flushing side arm and reverse flow/catheter receiving main arm disposed at the base ends thereof, flushing may be immediately begun through the side arm with heparinized saline and interrupted only when it is desired to record coronary pressures. A double lumen dilating catheter is then inserted past the reverse flow valve within the guide catheter, which dilating catheter itself is provided with two arms, one arm of which communicates with an open tipped inner lumen which receives a stylet having a preselected thickness which is substantially thinner than the inner lumen of the dilating catheter and the other arm of which communicates through an outer lumen with a balloon located near the catheter tip. This inner lumen of the dilating catheter is also continuously flushed with heparinized saline, except when recording coronary pressures. The outer lumen of the dilating catheter is used for injecting dye and saline for inflating the balloon during dilation. In the preferred embodiment, the stylet is threaded through the inner lumen of the dilating catheter to extend to within 3 to 5 mm. of the tip of the catheter. Similarly, in the preferred embodiment, the balloon is located approximately 1 cm. behind the tip of the dilating catheter so that the tip may be used to guide the dilating catheter through an obstruction. By continuously flushing with heparinized saline through both the outer and inner catheters, and by utilizing the aforementioned stylet within the inner of the aforementioned catheters, it is now possible to safely dilate the coronary arteries of a patient without completely heparinizing that patient, and to do so with substantially less risk and a substantially higher expected percentage of success.

BRIEF DESCRIPTION OF THE DRAWINGS

Further objects and a better understanding of the present invention will be apparent from the following description of the preferred embodiment taken in conjunction with the formal drawings, FIG. 1 is a schematic of a guide catheter used in the present invention;

FIG. 2 is a schematic of a double lumen dilating catheter for use in the present invention;

FIG. 3 is a schematic of the insertion of the guide catheter and dilating catheter into the blood vessel of the patient being treated.

DESCRIPTION OF THE PREFERRED EMBODIMENT

Although specific forms of the invention have been selected for illustration in the drawings, and the following description is drawn in specific terms for the purpose of describing these forms of the invention, this description is not intended to limit the scope of the invention which is defined in the appended claims.

In accordance with the method of the present invention, a guide catheter 100 is provided having a single lumen 101 defined therein. In the preferred embodiment, this guide catheter may be 80 to 100 cm. long and have an 8 or 9 French diameter which may, if desired terminate in a 6 French tip. The base of this catheter should be provided with a side arm such that two distinct conduits 102, 103 merge into the single lumen catheter 101 which is inserted into the patient's body. One of these side arms 102 is to be provided with a rubber check valve 104, such as a ball check valve, flapper valve, or other valve which will prevent fluids from being discharged out of the catheter, but will permit the insertion therethrough of a dilating catheter 200, as described more fully hereinafter. The other side arm 103 of the guide catheter 100 is adapted to establish fluid communication with the lumen of the guide catheter so that the guide catheter may be continuously flushed with heparinized saline throughout the entire dilation procedure, except when that flushing is periodically ceased in favor of using that conduit for the purpose of determing the hydraulic pressure within the lumen. In accordance with the preferred embodiment of the present invention, the main length of this guide catheter may be pre-formed into any of a number of different shapes, as are known to the art, depending upon whether the catheter is to be inserted from the right or left arm or leg.

In accordance with the preferred embodiment of the present invention, a double lumen dilating catheter 200 should be provided which is approximately 20 cm. longer than the aforementioned guide catheter 100. The preferred embodiment, a 90 cm. guide catheter should be paired with a 110 cm. dilating catheter or, alternatively, a 100 cm. guide catheter may be paired with a 120 cm. dilating catheter. In the preferred embodiment, the dilating catheter 200 has a 5 French diameter for 75 to 85% of its length, the remaining length of the guide catheter having a 3 French diameter. In the preferred embodiment, the double lumen catheter has an inner lumen 201 which is adapted to receive a stylet or wire 202, which wire has a diameter which is at least 1 French but not more than 2 French (preferably 1.5 French) smaller than the inner diameter of the inner guide catheter lumen. This guide wire 202 should extend to within 3 to 5 mm. from the tip 203 of the guide catheter, the dilation balloon 204 being located 0.75 to 1.25, preferably 1 cm., behind the tip, thereby leaving a slightly narrower dilating catheter tip available for use in guiding the dilation catheter through obstructions. In the preferred embodiment, the inner lumen 201 of the dilation catheter 200 is approximately 2 to 5 French, preferably 3 to 4 French in diameter. The stylet 202 is preferably fitted into the catheter in such a manner as to easily permit the introduction of heparinized saline into the columnar channel which is defined between the stylet or wire and the inner diameter of the inner lumen 201 of the dilation catheter. In accordance with the preferred embodiment of the present invention, the above-described single lumen guide catheter 100 is inserted so that the tip is positioned at about the coronery osteum (opening) which is within at least 20 cm., and preferably with 10 cm. of the blockage 300 to be dilated. At this point, utilizing the side arm 103 in this guide catheter, the flushing of the guide catheter lumen with heparinized saline is begun. Contrast agent (Renografin) can also be injected to obtain an anteriogram and for checking the position of the catheter tip. A double lumen ballon catheter 200 of the type described above is then fitted with the aforementioned stylet 202 and inserted through the ball check or one-way valve 104 in the guide catheter and threaded through the single lumen 101 of that guide catheter. At this point, flushing is begun around the stylet through the inner lumen 201 with heparinized saline. Contrast agent (Renografin) can also be injected to check the postion of the catheter tip. Due to the combination of components selected, the balloon tip may now be maneuvered so that it is located directly within the obstruction to be dilated, whereupon dye may be injected with saline through the conduit associated with the outer lumen 205 of the dilation catheter to momentarily inflate the balloon to clear the obstruction.

Once the obstruction has been cleared in accordance with the above-described method, the balloon may be deflated and the dilating catheter removed through the guide catheter, after which the guide catheter may be removed from the patient. During the entire process, it is preferred to continue flushing both catheters with heparinized saline except for periodic interruptions which may be desired for the purpose of checking coronary pressures, and periodic injection of contrast agents (Renografin) for determining the position of blockages in the coronary artery. In this manner, a substantial increase in the reliability and safety of coronary dilation techniques is provided by the method of the present invention.

It will be understood that various changes in the details, materials and arrangement of parts which have been herein described and illustrated in order to explain the nature of this invention may be made by those skilled in the art within the principle and scope of the invention as expressed in the following claims.

It will further be understood that the "Abstract of the Disclosure" set forth above is intended to provide a non-legal technical statement of the contents of the disclosure in compliance with the Rules of Practice of the United States Patent and Trademark Office, and is not intended to limit the scope of the invention described and claimed herein.

What is claimed is:

1. The method of dilating coronary arteries comprising the steps of:
    (a) providing a single lumen guide catheter;
    (b) providing first and second conduits at the base of said single lumen guide catheter, said first conduit being adapted to restrict the flow of liquid out of said catheter and to sealingly receive a dilation catheter therethrough, and said second conduit being adapted to receive a heparinization flushing fluid therethrough;
    (c) inserting said guide catheter through the circulatory system of a patient to within at least 20 cm of a coronary blockage to be dilated;
    (d) providing a double lumen balloon catheter sized for passage through said first conduit into the single lumen of said guide catheter, said double lumen balloon catheter being at least 10 cm longer than said guide catheter;
    (e) inserting a stylet into the inner lumen of said double lumen balloon catheter, said stylet extending within 3 to 5 mm of the tip of said balloon catheter;
    (f) inserting said double lumen balloon catheter into said single lumen guide catheter through said first conduit;
    (g) flushing the area around said stylet through the inner lumen of said double lumen balloon catheter with haparinization fluid;
    (h) manipulating the balloon portion of said double lumen balloon catheter to a point within said obstruction to be dilated; and
    (i) injecting dye and saline into said outer lumen of said double lumen catheter to at least temporarily inflate the balloon portion of said catheter, and thereby clear said obstruction.

2. The invention of claim 1 wherein said flushing of said guide catheter is periodically interrupted to measure the hydraulic pressure within said guide catheter lumen.

3. The invention of claim 1 wherein said flushing around said stylet through said inner lumen of said double lumen balloon catheter is periodically interrupted for the purpose of measuring the hydraulic pressure within said lumen.

4. The invention of claim 1 wherein said double lumen catheter is provided with a balloon which is disposed at a distance from the tip of said double lumen catheter which is between 0.75 and 1.25 cm. from that tip, and wherein that tip is utilized during said manipulating step to guide said balloon to within said obstruction.

5. The invention of claim 1 wherein said guide catheter is moved to within at least 10 cm. of said blockage.

* * * * *